(12) United States Patent
Sakurai et al.

(10) Patent No.: US 7,682,366 B2
(45) Date of Patent: Mar. 23, 2010

(54) CALCULUS MANIPULATION APPARATUS

(75) Inventors: Tomohisa Sakurai, Tokyo (JP); Koji Shimomura, Tokyo (JP); Shinji Hatta, Tokyo (JP); Naomi Sekino, Tokyo (JP); Hiroshi Okabe, Tokyo (JP); Hiroo Ono, Tokyo (JP); Tsuruo Hatori, Tokyo (JP); Takeaki Nakamura, Tokyo (JP)

(73) Assignee: Olympus Corporation (JP)

( * ) Notice: Subject to any disclaimer, the term of this patent is extended or adjusted under 35 U.S.C. 154(b) by 1183 days.

(21) Appl. No.: 10/685,060

(22) Filed: Oct. 14, 2003

(65) Prior Publication Data

US 2005/0033314 A1 Feb. 10, 2005

(30) Foreign Application Priority Data

Oct. 16, 2002 (JP) .............................. 2002-301993
Oct. 17, 2002 (JP) .............................. 2002-303398

(51) Int. Cl.
*A61B 17/22* (2006.01)
(52) U.S. Cl. ...................... 606/128; 606/169
(58) Field of Classification Search .............. 606/127, 606/128, 169
See application file for complete search history.

(56) References Cited

U.S. PATENT DOCUMENTS

| 3,805,787 | A | * | 4/1974 | Banko | 604/22 |
|---|---|---|---|---|---|
| 3,896,811 | A | | 7/1975 | Storz | 128/328 |
| 4,196,736 | A | * | 4/1980 | Watanabe | 606/128 |
| 4,486,680 | A | | 12/1984 | Bonnet et al. | 310/323 |
| 4,823,793 | A | | 4/1989 | Angulo et al. | 128/328 |
| 4,927,427 | A | | 5/1990 | Kriauciunas et al. | 606/128 |
| 5,403,324 | A | | 4/1995 | Ciervo et al. | 606/128 |
| 5,957,943 | A | * | 9/1999 | Vaitekunas | 606/169 |
| 5,989,274 | A | * | 11/1999 | Davison et al. | 606/169 |
| 6,695,834 | B2 | * | 2/2004 | Gellman et al. | 606/2.5 |
| 2002/0010486 | A1 | * | 1/2002 | Hirt | 606/169 |

FOREIGN PATENT DOCUMENTS

JP 60-96241 5/1985

(Continued)

OTHER PUBLICATIONS

Decision of Rejection issued Mar. 25, 2008 by Japanese Patent Office in connection with corresponding application No. 2002-301993 and English translation thereof submitted in lieu of statement of relevancy.

(Continued)

*Primary Examiner*—Todd E Manahan
*Assistant Examiner*—Michael G Mendoza
(74) *Attorney, Agent, or Firm*—Ostrolenk Faber LLP (57) ABSTRACT

An ultrasonic lithotripter comprising a first transmission probe which has a hollow portion in the form of a through hole and transmits ultrasonic vibration and a superfine second transmission probe which can be passed through the hollow portion of the first transmission probe. An object of manipulation is held by means of the second transmission probe as it is manipulated by means of the first transmission probe.

2 Claims, 9 Drawing Sheets

| | FOREIGN PATENT DOCUMENTS | |
|---|---|---|
| JP | 62-14843 | 1/1987 |
| JP | 62-144645 | 6/1987 |
| JP | 63-84215 | 6/1988 |
| JP | 63-84216 | 6/1988 |
| JP | 5-111493 | 5/1993 |
| JP | 5-184585 | 7/1993 |
| JP | 6-38804 | 5/1994 |
| JP | 3132972 | 11/2000 |
| JP | 2002-513646 | 5/2002 |
| WO | WO 01/01869 | 1/2001 |

OTHER PUBLICATIONS

Office Action issued by the Japanese Patent Office on Oct. 23, 2007 in connection with corresponding Japanese Patent Application No. 2002-301993.

Translation of Office Action issued by the Japanese Patent Office on Oct. 23, 2007 in connection with corresponding Japanese Patent Application No. 2002-301993.

* cited by examiner

CALCULUS MANIPULATION APPARATUS

CROSS-REFERENCE TO RELATED APPLICATIONS

This application is based upon and claims the benefit of priority from the prior Japanese Patent Applications No. 2002-301993, filed Oct. 16, 2002; and No. 2002-303398, filed Oct. 17, 2002, the entire contents of both of which are incorporated herein by reference.

BACKGROUND OF THE INVENTION

1. Field of the Invention

The present invention relates to a calculus manipulation apparatus capable of crushing and recovering an object of manipulation, such as a calculus in the body cavity, e.g., the kidney, ureter, urinary bladder, etc., by utilizing ultrasonic vibration.

2. Description of the Related Art

Conventionally, there are various surgical instruments that approach and remove a calculus in the urinary bladder or a ureter through the urethra (refer to Jpn. Pat. Appln. KOKOKU Publication No. 6-38804 (Patent Document 1), for example). A surgical instrument of Patent Document 1 uses an ultrasonic probe to crush a coral calculus that adheres to the kidney. Then, the calculus that is chipped away from the kidney is picked up in a basket and pulverized.

An ultrasonic calculus crusher, kinetic-energy lithotripter, electrohydraulic shock wave lithotripter, etc. are conventionally known as apparatuses that are inserted into the body cavity through a channel of an endoscope and crush a calculus. The ultrasonic calculus crusher crushes the calculus by means of the distal end of a lithotriptic probe that undergoes ultrasonic vibration. The kinetic-energy lithotripter uses compressed air or electromagnetic means to subject a probe to longitudinal vibration and crushes the calculus by utilizing the shock of the vibration. The electrohydraulic shock wave lithotripter crushes the calculus with shock waves based on electric discharge.

Figure 28:
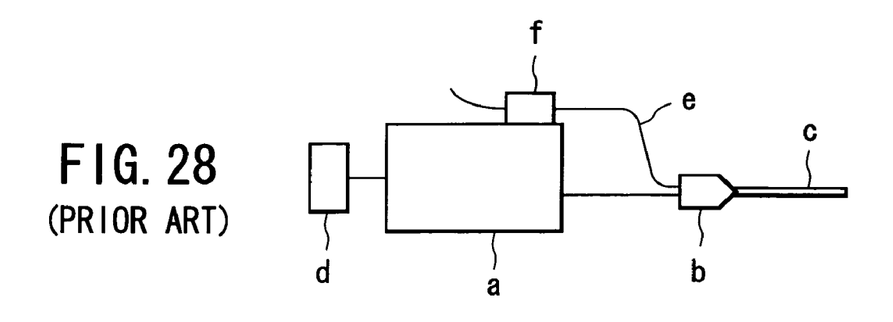
FIG. 28 is a schematic view of a conventional ultrasonic calculus crusher.

FIG. 28 shows an example of the ultrasonic calculus crusher. The ultrasonic calculus crusher comprises a high-frequency power source a, a vibrator b for converting high-frequency power from the power source a into ultrasonic vibration, and an elongate lithotriptic probe c of which the proximal end portion is connected to the vibrator b. The vibration generated by the vibrator b is propagated to the distal end side by means of the lithotriptic probe c. Further, a footswitch d is connected to the high-frequency power source a. A calculus is crushed by ultrasonic vibration in a manner such that the distal end portion of the lithotriptic probe c is brought into contact with the calculus with the probe c in a manipulation channel of the endoscope.

The vibrator b and the lithotriptic probe c are hollow. This hollow pipeline is connected to a suction tube e. The suction tube e is fitted with a roller pump f. In operation, the distal end portion of the lithotriptic probe c of the ultrasonic calculus crusher is brought into contact with the calculus. As this is done, the calculus is crushed by ultrasonic vibration, and at the same time, fragments of the calculus are sucked through the hollow pipeline.

Examples of the kinetic-energy lithotripter are described in Patent Specification No. 3132972 (Patent Document 2) and Jpn. Pat. Appln. KOKAI Publication No. 62-144645 (Patent Document 3). The apparatus of Patent Document 2 transmits a shock produced by compressed air to a lithotriptic probe and crushes a calculus by means of the distal end of the probe. The apparatus of Patent Document 3 transmits a shock produced by an electromagnetic method to a lithotriptic probe and crushes a calculus by means of the distal end of the probe.

Figure 29A:
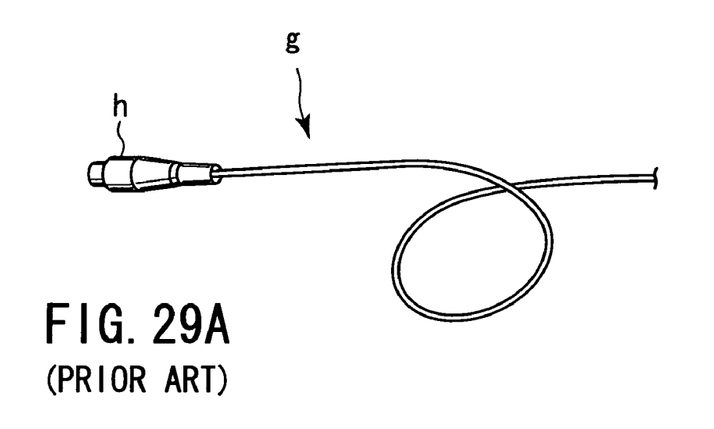
FIG. 29A is a perspective view showing a lithotriptic probe of a conventional electrohydraulic lithotripter.
Figure 29B:
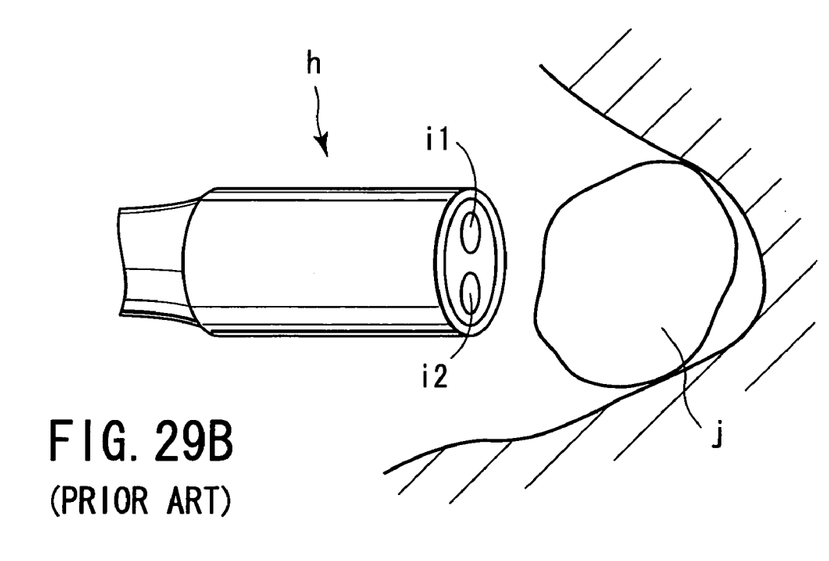
FIG. 29B is a perspective view showing the way of crushing a calculus.

FIG. 29A shows an example of the electrohydraulic lithotripter. This apparatus is provided with two electrodes i1 and i2 on a distal end portion h of a soft lithotriptic probe g, as shown in FIG. 29B. A calculus j is crushed with shock waves that are generated when electric discharge is caused between the electrodes i1 and i2.

According to alternative known methods (refer to Jpn. Pat. Appln. KOKAI Publication No. 60-96241 (Patent Document 4) and Jpn. Pat. Appln. KOKAI Publication No. 5-111493 (Patent Document 5), for example), a calculus is crushed mechanically by means of a basket forceps or by ultrasonic vibration. These methods cannot ensure a satisfactory crushing force.

Means for holding down a calculus is described in Jpn. UM Appln. KOKAI Publication No. 63-84215 (Patent Document 6) and Jpn. UM Appln. KOKAI Publication No. 63-84216 (Patent Document 7). This means efficiently applies shock waves to a calculus in crushing it and holds it down lest it move and hinder positioning of a probe for shock wave generation.

Described in Jpn. Pat. Appln. KOKAI Publication No. 62-14843 (Patent Document 8), moreover, is an example in which a sucker that is attached to the distal end of an endoscope channel is brought into contact with a calculus to suck it, whereby the calculus can be fixed in front of the channel during a lithotriptic operation.

BRIEF SUMMARY OF THE INVENTION

According to the present invention, there is provided a calculus manipulation apparatus, comprising: first and second ultrasonic generator elements which generate ultrasonic vibration; a first transmission probe having a proximal end portion connected to the first ultrasonic generator element and a hollow portion in the form of a through hole; a tip manipulator element which is provided on the distal end portion of the first transmission probe and brought into contact with a calculus, the tip manipulator element receiving ultrasonic vibration from the ultrasonic generator elements through the probe; and a second transmission probe capable of being passed through the hollow portion of the first transmission probe, the second probe having a piercer section on the distal end portion thereof to which ultrasonic vibration is transmitted from the second ultrasonic generator element and which is stabbed into the calculus and a calculus fixing section which fixes the calculus to the distal end portion.

Preferably, according to the invention, the calculus fixing section has means which stops the second ultrasonic generator element with the piercer section in the calculus.

Preferably, according to the invention, the calculus fixing section has a balloon fixed to the distal end of the second transmission probe.

Preferably, according to the invention, the second transmission probe has a hollow portion in the form of a through hole, the hollow portion being formed having a feed air channel for inflating the balloon.

Preferably, according to the invention, there is provided a calculus manipulation apparatus which manipulates a calculus in a ureter, comprising: an elongate sheath having a distal end portion to be inserted into the ureter; a staple removably attached to the distal end portion of the sheath, the staple moving in the direction of insertion of the sheath to grasp the calculus; control means on the hand side of the sheath which discharges the staple from the sheath; and calculus removal means which hitches the staple to the calculus in the ureter and removes the calculus.

Preferably, according to the invention, the apparatus further comprises a wire having one end portion attached to the staple and the other end portion extending toward the control means, and calculus removal means which removes the calculus by pulling the wire with the staple hitched and coupled to the calculus.

Preferably, according to the invention, there is provided a manipulation apparatus which manipulates a calculus in a ureter, comprising: an elongate sheath having a distal end portion to be inserted into the ureter; staple means removably attached to the distal end portion of the sheath, the staple means being movable in the direction of insertion of the sheath to be driven into the calculus; means which drives the staple means into the calculus; and calculus removal means which hitches the staple means to the calculus and removes the calculus.

Preferably, according to the invention, the driving means has means which vibrates the staple means with shock waves.

Preferably, according to the invention, the staple means has a rugged portion, and the driving means screws the rugged portion of the staple means into the calculus.

Preferably, according to the invention, there is provided a manipulation apparatus which manipulates a calculus in a lumen, comprising: a calculus capture tool used in combination with a lithotripter which crushes a calculus and having a calculus capturing section capable of capturing the calculus as an object of manipulation on the distal end portion of an insert section to be inserted into the lumen.

Preferably, according to the invention, the calculus capturing section has a helical member having an adjustable outside diameter.

Preferably, according to the invention, the calculus capture tool has regulating means which adjusts the outside diameter of the helical member so that the helical member is brought alternately into an extended state in which the outside diameter of the helical member is larger than the diameter of the calculus as the object of manipulation or a contracted state in which the helical member can capture the calculus.

Preferably, according to the invention, there is provided a calculus manipulation apparatus comprising: lithotriptic means which is passed through an endoscope channel and crushes a calculus; and fixing means which fixes the calculus in a position near the distal end of the endoscope channel.

Preferably, according to the invention, the lithotriptic means has a lithotriptic probe, and the fixing means has a bundle of linear members, each of the linear members having a bent tip portion centripetally bent inward, the linear member bundle being movable in the axial direction of the endoscope channel with the linear members arranged in the shape of a cylinder in the endoscope channel, the lithotriptic probe being passed through the cylinder of the linear member bundle.

Preferably, according to the invention, the linear members have an expanded shape such that at least the bent tip portions are spread to a diameter larger than the inside diameter of the endoscope channel when the linear members project outward from the endoscope channel.

Preferably, according to the invention, there is provided a calculus manipulation apparatus comprising: lithotriptic means which crushes a calculus through an endoscope channel; a helical member having a variable diameter and situated on the distal side of the endoscope channel; a control member having one end portion connected to at least one end of the helical member and the other end portion extending to the proximal end of the endoscope channel and capable of manipulating the helical member on the proximal side of the endoscope channel; calculus holding means which operates the control means to hold the calculus in the helical member; and means which causes the lithotriptic means to project from the distal end of the endoscope channel so as to run against the calculus, thereby crushing the calculus.

Preferably, according to the invention, the helical member is loaded with a shape memory such that the helical member becomes helical when heated to a preset or higher temperature.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

An ultrasonic lithotripter according to a first embodiment of the present invention will now be described with reference to FIGS. 1 and 2. The ultrasonic lithotripter of the present embodiment comprises a grip section 1. The grip section 1 has therein an ultrasonic generator element 2 for lithotripsy that is composed of a vibrator. The proximal end portion of a hollow first transmission probe 3 is connected mechanically to the ultrasonic generator element 2 by means of a horn (not shown). An ultrasonic manipulator element 3b is provided on the distal end of the first transmission probe 3.

A power supply unit (not shown) is connected to the ultrasonic generator element 2 by means of a power cord 4. In starting operation, electrical energy is supplied from the power supply unit to the ultrasonic generator element 2 for lithotripsy. The ultrasonic generator element 2 converts the electrical energy into ultrasonic vibration. This ultrasonic vibration is transmitted through the hollow transmission probe 3 to the manipulator element 3b at the distal end.

A hollow pipeline 5 linearly penetrates the ultrasonic generator element 2 of the grip section 1 in its longitudinal direction. The distal end portion of the pipeline 5 communicates with a hollow hole 3a of the transmission probe 3. A suction port 7 protrudes from the outer peripheral surface of the grip section 1. The inner end portion of the suction port 7 is connected to the middle portion of the hollow pipeline 5 of the grip section 1. A suction tube (not shown) is connected to the outer end portion of the suction port 7. The suction tube is connected to a suction pump (not shown).

An inlet port 9 is attached to the rear end portion of the grip section 1. It communicates with the proximal end portion of the hollow pipeline 5 of the ultrasonic generator element 2 for lithotripsy. A superfine transmission probe (second transmission probe) 8 for calculus retention can be inserted into the grip section 1 through the inlet port 9. The inlet port 9 is provided with seal means such as a rubber cap member (not shown). When the transmission probe 8 is inserted into the inlet port 9, the seal means seals the port 9 lest air leak through it. This seal means prevents retardation of the function for suction through the suction port 7.

A grip section 11 is connected to the hand side of the superfine transmission probe 8. The grip section 11 has a superfine ultrasonic generator element 10 therein. The generator element 10 is connected to the power supply unit (not shown) by means of a power cord 12. Electrical energy that is supplied from the power supply unit is converted into ultrasonic vibration by means of the generator element 10. The ultrasonic vibration is transmitted through the superfine transmission probe 8 to a manipulator element at the distal end.

Figure 1:
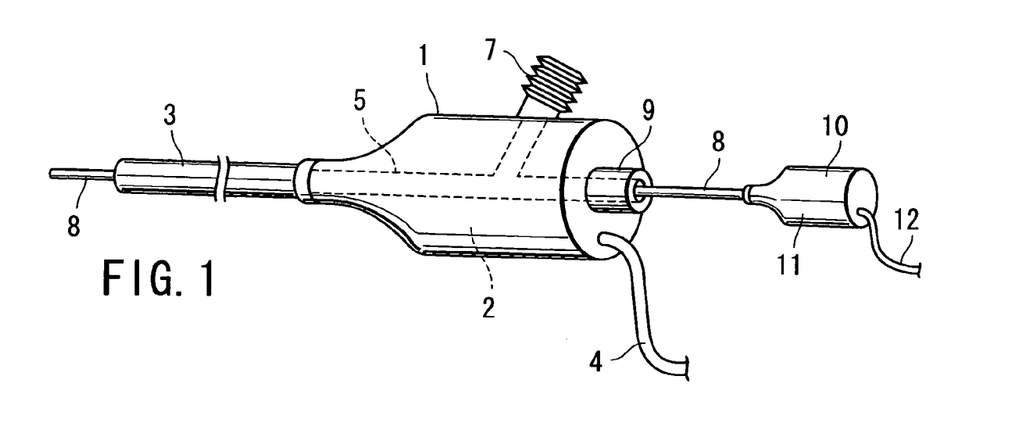
FIG. 1 is a perspective view of an ultrasonic lithotripter according to a first embodiment of the invention.
Figure 2:
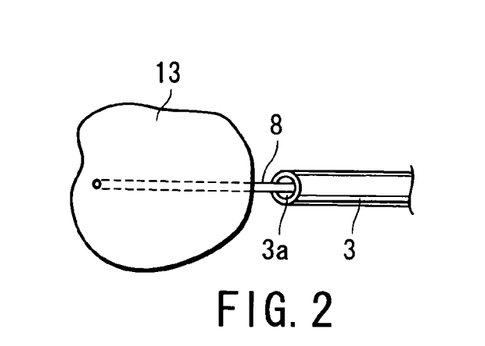
FIG. 2 is a view illustrating the way the ultrasonic lithotripter of the first embodiment is used.

As shown in FIG. 1, moreover, the superfine transmission probe 8 is inserted through the inlet port 9 and caused to project forward from the distal end of the transmission probe 3 through the hollow pipeline 5 of the grip section 1 and the hollow hole 3a of the probe 3.

The following is a description of the way of using the ultrasonic lithotripter. First, the transmission probe 3 of the lithotripter is inserted into the body cavity. Thereafter, the superfine transmission probe 8 is inserted into the probe 3 through the inlet port 9. As this is done, the probe 8 is guided from the hollow pipeline 5 of the grip section 1 to the distal end side through the hollow hole 3a of the transmission probe 3.

The superfine ultrasonic generator element 10 is driven to subject the superfine transmission probe 8 to ultrasonic vibration as the probe 8 is pressed against a calculus 13. Since the probe 8 undergoes ultrasonic vibration as this is done, its distal end portion easily pierces through the calculus 13 and is embedded in it.

When the distal end portion of the superfine transmission probe 8 pierces to a certain depth, the ultrasonic vibration is stopped. Thereupon, the calculus 13 is fixed to the probe 8.

After the calculus 13 is fixedly coupled to the superfine transmission probe 8, the transmission probe 3 is subjected to ultrasonic vibration as it advances. If the distal end of the transmission probe 3 is held against the calculus 13 in this state, the calculus 13 can be crushed.

According to the ultrasonic lithotripter of the present embodiment, the calculus 13 can be fixed to the superfine transmission probe 8. The calculus 13 is kept fixed to the probe 8 as it is subjected to ultrasonic lithotripsy by means of the transmission probe 3. During ultrasonic lithotripsy by means of the transmission probe 3, therefore, there is no possibility of the calculus 13, as an object of manipulation, escaping further inward from the transmission probe 3. In consequence, the ultrasonic vibration can be efficiently applied to the calculus 13, so that the capability to crush the calculus 13 can be improved.

Figure 3:
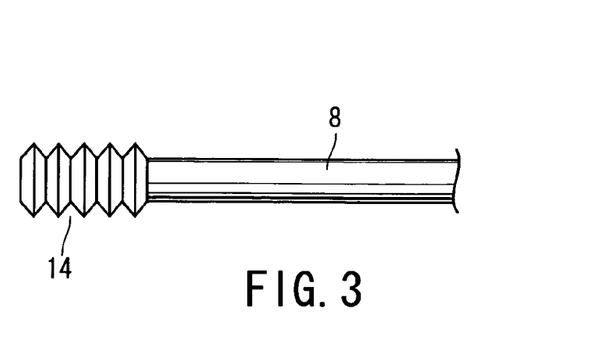
FIG. 3 is a side view showing the principal part of a modification of a superfine transmission probe of the ultrasonic lithotripter of the first embodiment.

FIG. 3 shows a modification of the ultrasonic lithotripter of the first embodiment. According to this modification, knurled teeth 14 are provided on the outer peripheral surface of the distal end portion of the superfine transmission probe 8 by alternately forming annular grooves and ridges thereon or by threading the outer peripheral surface. By doing this, the force to fix the calculus 13 to the probe 8 can be enhanced.

Figure 4:
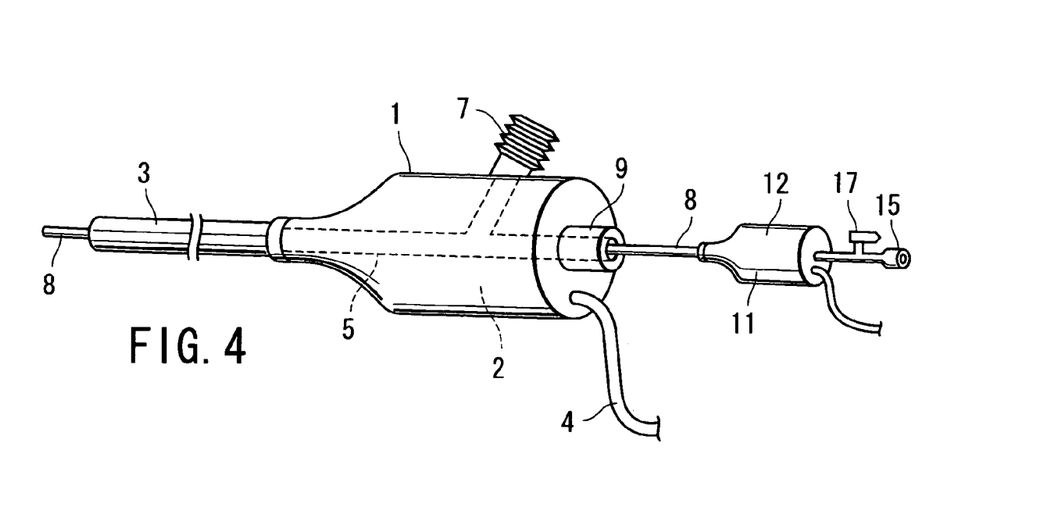
FIG. 4 is a perspective view of an ultrasonic lithotripter according to a second embodiment of the invention.
Figure 5:
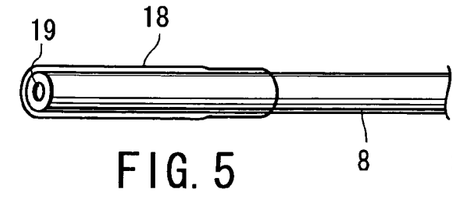
FIG. 5 is a perspective view of a superfine transmission probe of the ultrasonic lithotripter of the second embodiment.
Figure 6:
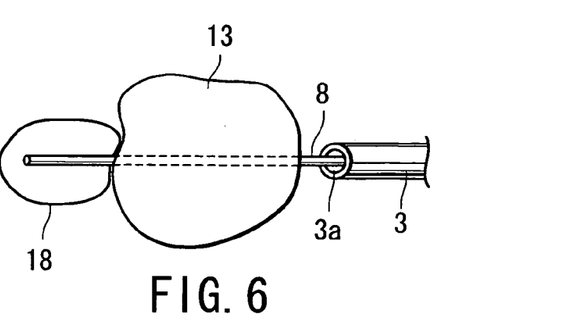
FIG. 6 is a view illustrating the way the ultrasonic lithotripter of the second embodiment is used.

FIGS. 4 to 6 show an ultrasonic lithotripter according to a second embodiment of the invention. A superfine transmission probe 8 according to the present embodiment is a modification of the superfine transmission probe 8 for calculus retention according to the first embodiment (see FIGS. 1 and 2). The ultrasonic lithotripter of the second embodiment shares other components with the ultrasonic lithotripter of the first embodiment. Therefore, like numerals are used to designate like components, and a repeated description of those components is omitted.

The superfine transmission probe 8 of the present embodiment is in the form of a hollow pipe. A grip section 11 of the probe 8 is provided with a syringe mounting hole 15 and a faucet portion 17 at its rear end. A syringe (not shown) can be attached to the mounting hole 15. The faucet portion 17 is used to connect or disconnect the mounting hole 15 and a hollow pipeline 16 of the probe 8.

As shown in FIG. 5, moreover, an elastic balloon 18 is provided on the outer periphery of the distal end of the superfine transmission probe 8. The balloon 18 can be inflated with air that is fed through a hollow portion 19 of the probe 8.

In operating this ultrasonic lithotripter, the balloon 18 is first deflated in advance, as shown in FIG. 5. In this state, the superfine transmission probe 8 is subjected to ultrasonic vibration as the calculus 13 is pierced with it. When this is done, the probe 8 is inserted so that its distal end portion having the balloon 18 therein penetrates the calculus 13. Thereafter, the syringe is used to feed air through the syringe mounting hole 15 of the superfine ultrasonic generator element 10, thereby inflating the balloon 18, as shown in FIG. 6. Thereafter, the faucet portion 17 is closed.

The inflated balloon 18 can prevent the calculus 13 from getting away inward from the transmission probe 3 for manipulation. Thus, the superfine transmission probe 8 and the calculus 13 can be fixed more securely. In this state, lithotriptic operation is carried out by means of the transmission probe 3.

In the present embodiment, the balloon 18 covers the distal end portion of the superfine transmission probe 8 including the distal opening of the hollow portion 19 of the probe 8. Alternatively, the distal opening of the hollow portion 19 may be sealed. If this is done, an aperture is formed in the sidewall of the distal end portion of the probe 8 so that the probe 8 can internally connect with the balloon 18 by means of the aperture. In this case, the distal end of the probe 8 may be designed to be exposed forward through the balloon 18. Thus, the distal end of the probe 8 can be held directly against the calculus 13.

Figure 7:
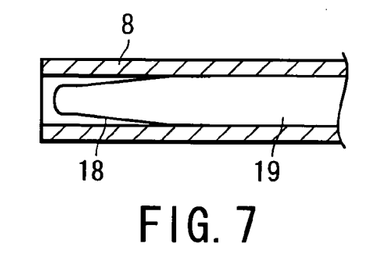
FIG. 7 is a longitudinal sectional view of the distal end portion of a superfine transmission probe of an ultrasonic lithotripter according to a third embodiment of the invention.
Figure 8:
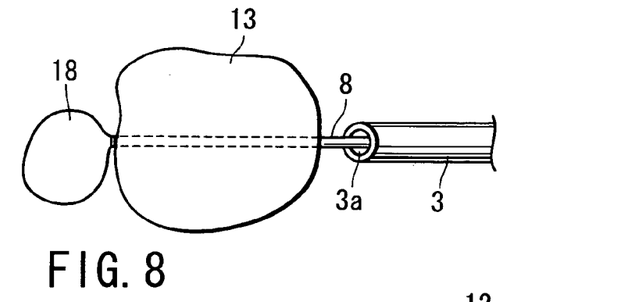
FIG. 8 is a view illustrating the way the ultrasonic lithotripter of the third embodiment is used.

FIGS. 7 and 8 show an ultrasonic lithotripter according to a third embodiment of the invention. The present embodiment is a modification of a structure for mounting a balloon 18 on the distal end portion of a superfine transmission probe 8 for calculus retention. The ultrasonic lithotripter of the third embodiment shares other components with the ultrasonic lithotripters of the first embodiment (see FIGS. 1 and 2) and the second embodiment (see FIGS. 4 to 6). Therefore, like numerals are used to designate like components, and a repeated description of these components is omitted.

The superfine transmission probe 8 of the present embodiment, like that of the second embodiment, is in the form of a hollow pipe. As shown in FIG. 7, an inflatable elastic balloon 18 is located in the distal end portion of a hollow portion 19 of the probe 8. Normally, the balloon 18 is deflated as it is drawn into the hollow portion 19 to be stored therein, as shown in FIG. 7. The balloon 18 is inflated with air that is fed through the hollow portion 19. Thus, the balloon 18 can inflate after it gets out of the distal end of the probe 8, as shown in FIG. 8.

In operating this ultrasonic lithotripter, the superfine transmission probe 8 is subjected to ultrasonic vibration as the calculus 13 is pierced with it. When this is done, the probe 8 is inserted so that its distal end portion having the balloon 18 therein penetrates the calculus 13. Thereafter, a syringe is used to feed air through a syringe mounting hole 15 of a superfine ultrasonic generator element 10.

As air is fed into the balloon 18, the balloon 18 exits the distal end of the superfine transmission probe 8 and inflates, as shown in FIG. 8. Thereafter, a faucet portion 17 is closed.

Thus, the balloon 18 can securely fix the calculus 13 to the superfine transmission probe 8 lest the calculus 13 slip out of the probe 8. In consequence, the calculus 13 can be prevented from escaping inward from a transmission probe 3 for manipulation. In this state, lithotriptic operation is carried out by means of the hollow transmission probe 3.

As the superfine transmission probe 8 is inserted into the calculus 13, according to the present embodiment, the balloon 18 can be kept in the hollow portion 19. Accordingly, there is no possibility of the balloon 18 being damaged by friction with the calculus 13 or the like.

Figures 9, 10:
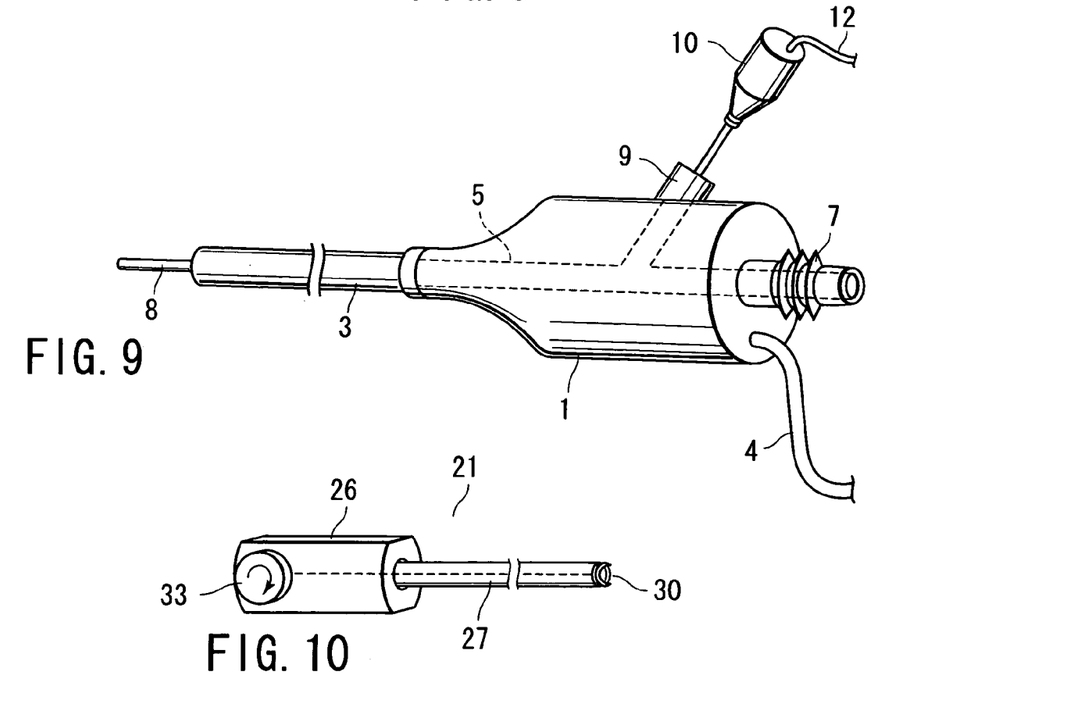
FIG. 9 is a perspective view of an ultrasonic lithotripter according to a fourth embodiment of the invention.
FIG. 10 is a perspective view of a calculus collector used in combination with a ureteroscope according to a fifth embodiment of the invention.

FIG. 9 shows an ultrasonic lithotripter according to a fourth embodiment of the invention. According to the present embodiment, a transmission probe 3 for calculus manipulation is modified. The ultrasonic lithotripter of the fourth embodiment shares other components with the ultrasonic lithotripter of the first embodiment. Therefore, like numerals are used to designate like components, and a repeated description of those components is omitted.

In the present embodiment, the respective positions of a suction port 7 and an inlet port 9 of a grip section 1 are changed. More specifically, the suction port 7 is set on the rear end portion of the grip section 1, and the inlet port 9 on the lateral portion of the grip section 1. Naturally, both the suction port 7 and the inlet port 9 communicate with a hollow pipeline 5 of the grip section 1. A superfine transmission probe 8 is formed as a softer probe that can be inserted into the pipeline 5 through the lateral inlet port 9.

The ultrasonic lithotripter of the present embodiment is operated in the same manner as the lithotripter of the first embodiment. According to the present embodiment, a suction pipeline that extends from a hollow transmission probe 3 to the suction port 7 through the hollow pipeline 5 is straight. Therefore, the crushed calculus 13 to be sucked cannot easily jam in the suction pipeline.

FIGS. 10 to 13 show a fifth embodiment of the invention. A calculus catcher 21 is used as a calculus collector that can discharge a staple through its sheath. The calculus catcher 21 is used in combination with a ureteroscope 20 (shown in FIG. 11).

As shown in FIG. 10, the calculus catcher 21 comprises a control section 26 for use as control mechanism means on the proximal side of the sheath and an insert section 27 in the form of a flexible sheath. The insert section 27 can be passed through a channel of the ureteroscope 20.

Figure 12:
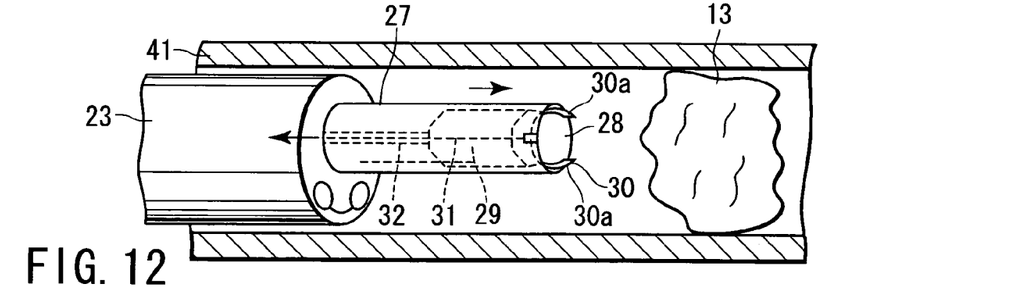
FIG. 12 is a view illustrating the way the manipulator of the fifth embodiment is used.

As shown in FIG. 12, a staple anchoring portion 28 is provided at a position corresponding to the extreme end of the insert section 27 of the calculus catcher 21. A staple clamper 29 is located just behind the anchoring portion 28. A staple 30 is removably attached to the anchoring portion 28.

Figure 13:
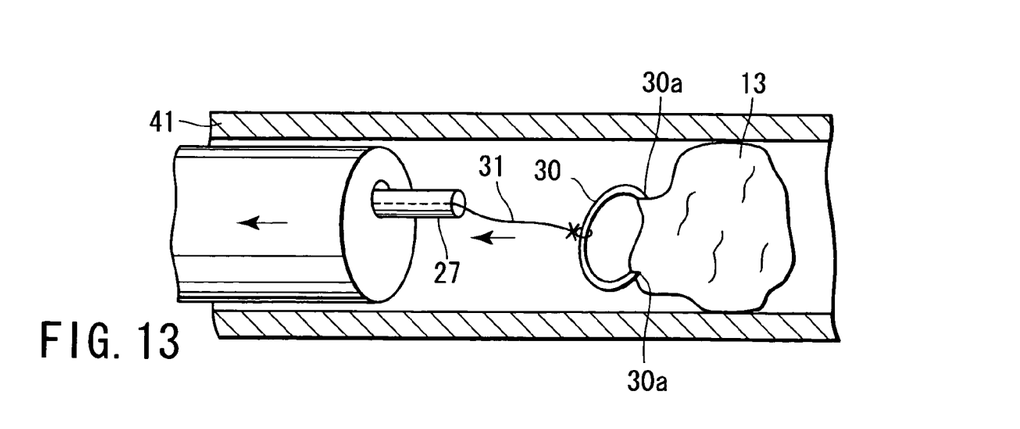
FIG. 13 is a view illustrating the way the manipulator of the fifth embodiment is used.

As shown in FIG. 13, the staple 30 is formed of a C-shaped wire. The opposite end portions of this wire individually form claws 30a that bite the calculus 13. Normally, the claws 30a of the staple 30 are open.

The staple 30 is attached to the staple anchoring portion 28 in a manner such that the open end claws 30a project from the extreme end of the insert section 27 of the calculus catcher 21. The staple clamper 29 is formed of a cylindrical member that catches the middle part of the staple 30. The staple 30 can be oriented as specified by settling a portion that catches the middle part of the staple 30 in a fixed posture.

Further, the distal end of a wire 31 for traction is fastened to the middle part of the staple 30. A passage hole 32 is formed in the insert section 27 of the calculus catcher 21. The wire 31 is guided into the catch control section 26 through the passage hole 32 and coupled to a traction control device.

The traction control device has a drum (not shown) that is rotated by operating a knob 33 or rotating handle, for example. The wire 31 can be pulled by winding the wire 31 on the drum. The middle part of the staple 30 is drawn in by pulling the wire 31 in a manner such that the staple 30 engages the staple clamper 29 and is attached to the staple anchoring portion 28. In consequence, the middle part of the staple 30 is transformed, whereupon the open claws 30a at its opposite ends can be closed.

Figure 11:
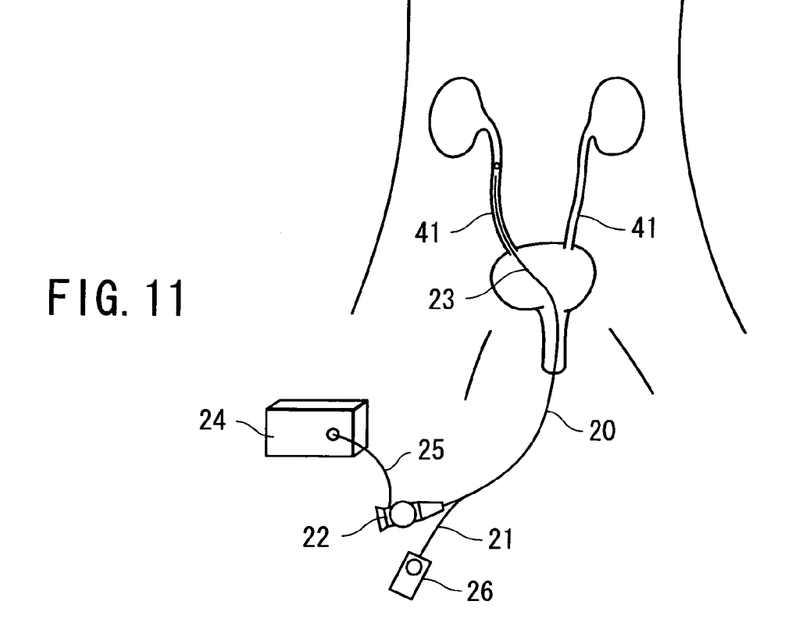
FIG. 11 is a view illustrating the way and the insert section of the ureteroscope of the fifth embodiment is inserted into a ureter to reach the position of a calculus.

As shown in FIG. 11, the ureteroscope 20 comprises a hand control section 22 and an insert section 23 that can be inserted into a ureter. One end portion of a light guide cable 25 is coupled to the control section 22. The other end portion of the cable 25 can be connected to an endoscopic light source unit 24.

The following is a description of the operation of the calculus catcher 21 constructed in this manner. In starting the operation of the calculus catcher 21, the insert section 23 of the ureteroscope 20 is inserted in advance into a ureter 41 so that it reaches the position of the calculus 13, as shown in FIG. 11.

Subsequently, the insert section 27 of the calculus catcher 21 that is fitted with the staple 30 is guided to the position of the calculus 13 in the ureter 41 through the channel of the ureteroscope 20, as shown in FIG. 12. Further, the staple 30 that is attached to the distal end portion of the insert section 23 of the calculus catcher 21 is brought close to and run against the calculus 13.

In this state, the knob 33 or rotating handle of the catch control section 26 is operated to pull the wire 31. Thereupon, the middle part of the staple 30 that is attached to the staple anchoring portion 28 is pressed by the staple clamper 29 and transformed. As this is done, the wide-open claws 30a at the opposite ends are closed to bite the calculus 13, whereupon the staple 30 is anchored to the calculus 13.

Thereafter, the staple 30 is further pulled by means of the wire 31. As this is done, the staple 30 is clamped by means of the staple clamper 29 so that it bites the calculus 13. In this state, the entire ureteroscope 20 is drawn out of the ureter 41. Thus, the calculus 13 can be taken out from the ureter 41 into the urinary bladder or to the outside of a patient's body.

According to the calculus catcher 21 constructed in this manner, the calculus 13 can be securely seized and removed without getting away toward the kidney.

Figure 14:
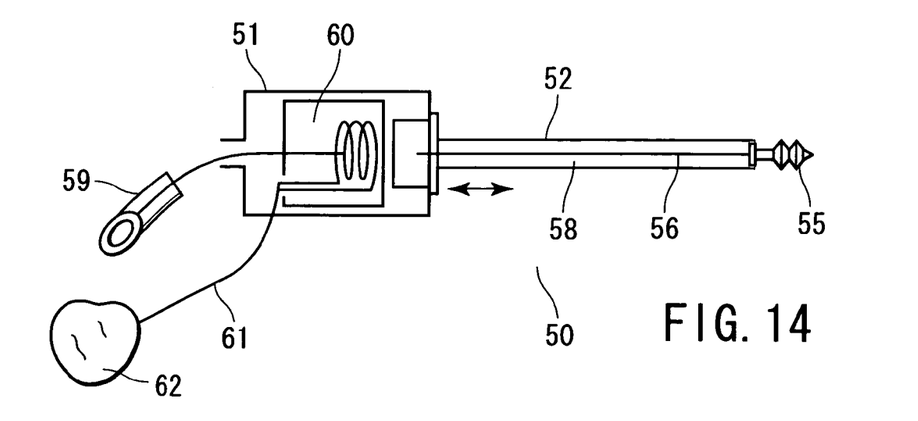
FIG. 14 is a perspective view of another calculus collector used in combination with a ureteroscope according to a sixth embodiment of the invention.
Figure 15:
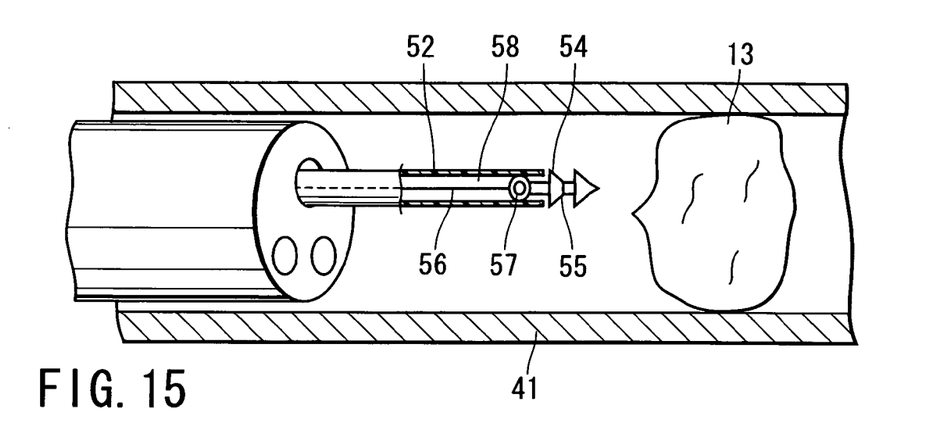
FIG. 15 is a view illustrating the way the manipulator of the sixth embodiment is used.
Figure 16:
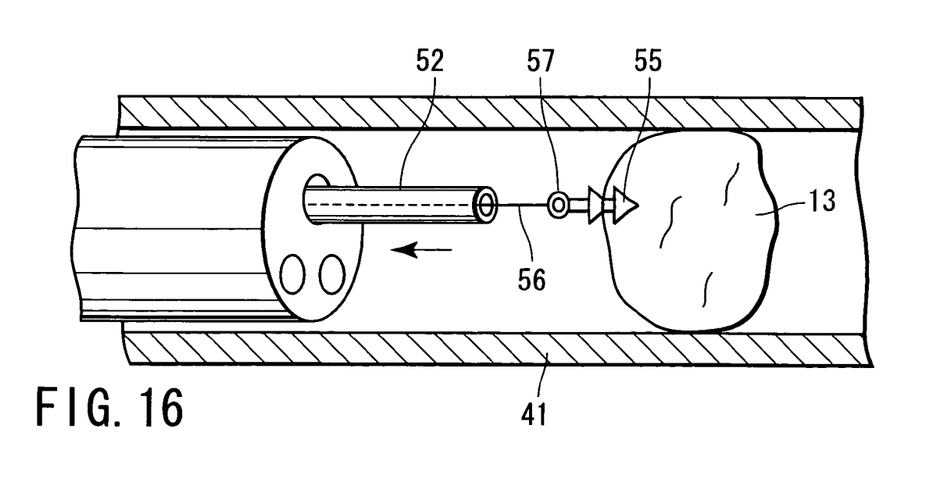
FIG. 16 is a view illustrating the way the manipulator of the sixth embodiment is used.

FIGS. 14 to 16 show a sixth embodiment of the invention. FIG. 14 shows an outline of a calculus catcher 50 in an alternative form that is used in combination with the ureteroscope 20. The calculus catcher 50 comprises a catch control section 51 and a soft hollow transmission pipe 52 for use as a flexible insert section. The transmission pipe 52 can be passed through a channel of the ureteroscope 20.

A staple anchoring portion 54 is provided at the extreme end of the transmission pipe 52 of the calculus catcher 50. A staple 55 is removably attached to the anchoring portion 54.

The staple 55 is formed of a jagged peg having knurled teeth or the like. A ring 57 for fastening the distal end portion of a wire 56 is formed on the proximal end of the staple 55.

When the staple 55 is removably attached to the staple anchoring portion 54, as shown in FIG. 15, it is set so that its sharp distal end portion projects from the distal end of the transmission pipe 52.

As shown in FIG. 14, moreover, a channel 58 is formed in the soft elongate transmission pipe 52 of the calculus catcher 50. The proximal end portion of the wire 56 that is coupled to the ring 57 of the staple 55 is guided through the channel 58 to the catch control section 51 of the calculus catcher 50, and is further guided through the control section 51 to the hand side. A control knob 59 is connected to the hand side of the wire 56. The knob 59 enables an operator to pull the wire 56.

As shown in FIG. 14, the catch control section 51 of the calculus catcher 50 is provided with an impact vibration generator element 60. The generator element 60 is connected to an external power supply unit 62 by means of a power cord 61. Impact vibrations that are generated by the generator element 60 are transmitted through the transmission pipe 52 to the staple 55 that is attached to the staple anchoring portion 54.

The following is a description of the operation of the calculus catcher 50 constructed in this manner. In starting the operation of the calculus catcher 50, the insert section 23 of the ureteroscope 20 is inserted in advance into the ureter 41 so that it reaches the position of the calculus 13, as shown in FIG. 11. Thereafter, the transmission pipe 52 of the calculus catcher 50 that is fitted with the staple 55 is inserted into the patient's body through the channel of the ureteroscope 20. As this is done, the distal end portion of the transmission pipe 52 is thrust out into the ureter 41 through the distal end of the ureteroscope 20 and brought close to the calculus 13, as shown in FIG. 15.

Then, the impact vibration generator element 60 is actuated to transmit impact vibrations to the peglike staple 55 through the transmission pipe 52. In this state, the staple 55 on the distal end of the transmission pipe 52 is caused to engage the calculus 13. As the staple 55 then undergoes impact vibration, it bites the calculus 13 (see FIG. 16).

Thereafter, the wire 56 is pulled to the hand side with the calculus 13 held in position, and the entire ureteroscope 20 is drawn out of the ureter 41. By doing this, the calculus 13 can be taken out to the outside of the patient's body or into the urinary bladder.

According to the calculus catcher 50 constructed in this manner, the calculus 13 can be securely gripped and removed from the ureter 41 without it escaping toward the kidney.

Figure 17A:
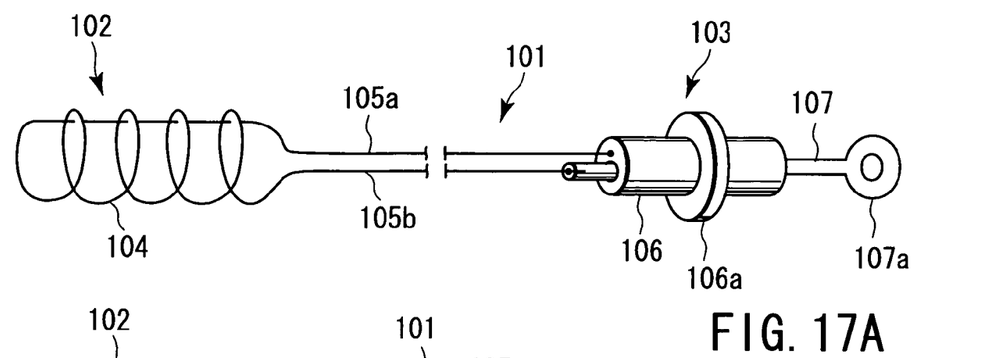
FIG. 17A is a perspective view showing an outline of a calculus capturing forceps according to a seventh embodiment of the invention.

FIGS. 17A and 17B and FIGS. 18A and 18B show a seventh embodiment of the invention. FIG. 17A shows a calculus capturing forceps 101 as a capture tool according to the present embodiment. The calculus capturing forceps 101 is inserted into the patient's body through a channel of an endoscope, and is used in combination with a lithotripter for crushing calculus. The calculus capturing forceps 101 has a calculus capturing section 102 on the distal end side and a hand control section (regulating means) 103 on the proximal end side.

The calculus capturing section 102 is provided with a helical tip member 104 that is formed by helically winding a wire, for example. The helical portion of the tip member 104 should only have two or more turns or loops, preferably two to four loops.

The distal end portion of a first linear control section 105a is connected to that of the helical tip member 104. Further, the distal end portion of a second linear control section 105b is connected to the proximal end portion of the tip member 104. The helical tip member 104 and the two linear control sections 105a and 105b may be formed by bending a single wire.

The hand control section 103 is provided with a substantially tubular control section body 106 and a control rod 107. The control rod 107 can be inserted into the lumen of the control section body 106. It is slidable in its axial direction and rotatable around its axis.

A flange-shaped finger support 106a protrudes from the outer peripheral surface of the control section body 106. The proximal end portion of the first linear control section 105a is fixed to the distal end face of the control section body 106.

A ring-shaped finger knob 107a is formed on the proximal end portion of the control rod 107. Further, the proximal end portion of the second linear control section 105b is fixed to the distal end portion of the rod 107.

Figure 17B:
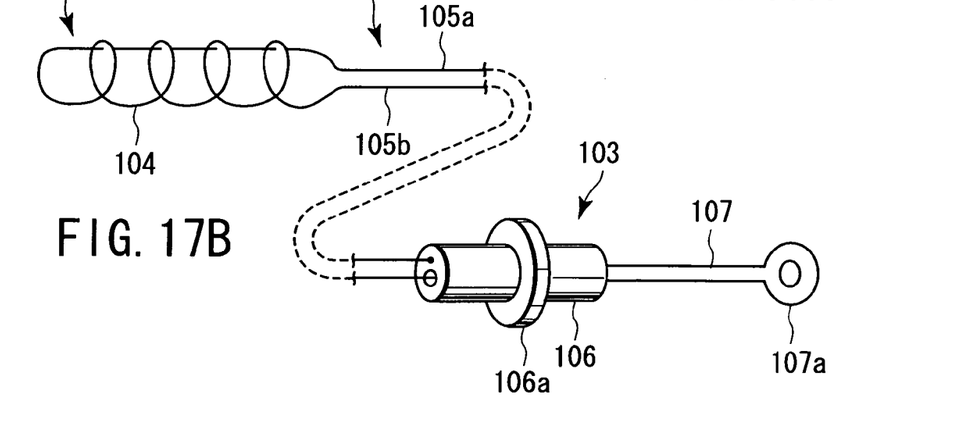
FIG. 17B is a perspective view showing the way a calculus capturing forceps according to the seventh embodiment is operated.

The hand control section 103 pulls the control rod 107 to the hand side with respect to the control section body 106, as shown in FIG. 17B, or pushes out the control rod 107 to the distal end side, as shown in FIG. 17A. Thus, the relative positions of the two linear control sections 105a and 105b are changed to extend or contract the helical tip member 104. Further, the control rod 107 is rotated clockwise or counterclockwise around the axis with respect to the control section body 106 of the hand control section 103. Thus, the helical member 104 can be wound up or loosened.

More specifically, the relative positions of the two linear control sections 105a and 105b in their length direction can be changed to increase or decrease the diameter of the helical portion of the helical tip member 104 by axially sliding the control rod 107 with respect to the control section body 106 of the hand control section 103. For example, the second linear control section 105b is moved to the hand side with respect to the first linear control section 105a by pulling the control rod 107 to the hand side with respect to the control section body 106, as shown in FIG. 17B. As the proximal end portion of the helical tip member 104 is then pulled to the hand side, the diameter of the helical portion of the tip member 104 is reduced.

Figures 18A, 18B:
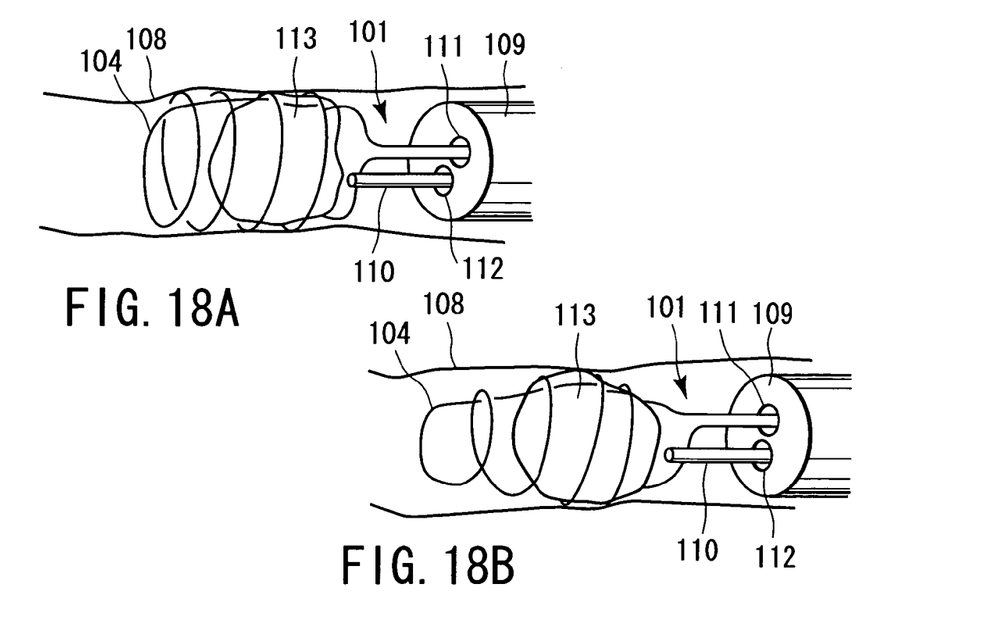
FIG. 18A is a view for illustrating the way a calculus is secured in a helical member as the calculus capturing forceps of the seventh embodiment is actually used.
FIG. 18B is a view for illustrating the way the helical member is narrowed to capture the calculus.

The following is a description of the operation of the configuration described above. FIGS. 18A and 18B show a situation in which the calculus capturing forceps 101 according to the present embodiment is actually used. In this situation, the calculus capturing forceps 101 and an ultrasonic lithotriptic probe 110 are inserted after a ureteroscope (endoscope) 109 is inserted in advance into a ureter 108. The ureteroscope 109 is provided with two instrument passage channels 111 and 112. The forceps 101 and the probe 110 are inserted in the channels 111 and 112, respectively. The forceps 101 and the probe 110 may be inserted into one and the same instrument passage channel.

In crushing a calculus 113 in the ureter 108, the calculus capturing forceps 101 is inserted into the one instrument passage channel 111, and the control rod 107 is then pushed out to the distal end side with respect to the control section body 106, as shown in FIG. 17A. Thereupon, the diameter of the helical tip member 104 is increased. In this state, the helical member 104 is held against the calculus 113 in the ureter 108 as the calculus 113 is guided into it.

After the calculus 113 is held in the helical member 104, moreover, the control rod 107 is pulled to the hand side with respect to the control section body 106 of the hand control section 103. Thus, the helical portion of the tip member 104 is narrowed to capture the calculus 113 therein, as shown in FIG. 18B.

The relative positions of the helical member 104 and the two linear control sections 105a and 105b are set so that the captured calculus 113 can be fixed in front of the instrument passage channel 111 of the ureteroscope 109 by pulling the calculus capturing forceps 101 to the hand side.

Thereafter, the ultrasonic lithotriptic probe 110 is inserted into the instrument passage channel 112 of the ureteroscope 109 to crush the calculus 113 that is fixed in the helical member 104 in front of the instrument passage channel 111 of the ureteroscope 109.

The above-described configuration produces the following effects. The calculus capturing forceps 101 of the present embodiment is provided with the helical member 104 and the hand control section 103. The helical member 104 is located in the calculus capturing section 102, and its outside diameter is adjustable. The control section 103 adjusts the outside diameter of the helical member 104 so that the member 104 is brought alternately to an extended or contracted state. In the extended state, the outside diameter of the helical member 104 is larger than the diameter of the calculus 113 as an object of manipulation. In the contracted state, the member 104 can hold the calculus 113. The calculus 113 can be kept fixed until it is pulverized by means of the ultrasonic lithotriptic probe 110 in a manner such that it is fixed in the helical member 104 in front of the instrument passage channel 111 of the ureteroscope 109 by the aforesaid method. Thus, the calculus 113 can be prevented from being moved by a shock without being crushed during the lithotriptic operation.

Further, there is no possibility of the calculus 113 being moved away from the ureteroscope 109 by the lithotriptic shock and requiring extra time for repeated approach. Thus, the lithotriptic operation can be carried out efficiently. In consequence, the calculus 113 can be easily crushed by using lithotriptic means such as the ultrasonic lithotriptic probe 110 in a manner such that the calculus 113 is held near the distal end portion of the endoscope channel when it is crushed endoscopically. Further, the calculus 113 can be prevented from being caused to slip off by the lithotriptic shock, so that the lithotriptic operation can be carried out more efficiently.

Figure 19A:
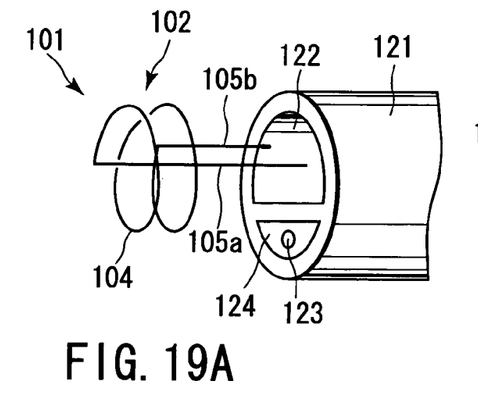
FIG. 19A is a perspective view of the principal part of a fixing portion between a helical member of a calculus capturing forceps according to an eighth embodiment of the invention and an endoscope.
Figure 19B:
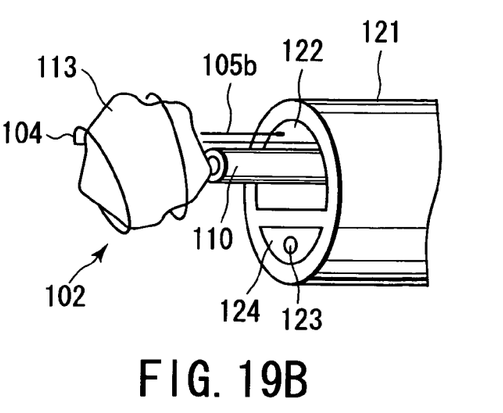
FIG. 19B is a perspective view of the principal part showing a calculus captured in the helical member of the calculus capturing forceps of the eighth embodiment.

FIGS. 19A and 19B show an eighth embodiment of the invention. According to the present embodiment, the configuration of the calculus capturing forceps 101 of the seventh embodiment (see FIGS. 17A and 17B and FIGS. 18A and 18B) is modified as in the following manner.

In the present embodiment, the proximal end portion of the second linear control section 105b of the calculus capturing forceps 101 of the seventh embodiment is fixed to the distal end portion of an endoscope 121. One instrument passage channel 122 is formed in the endoscope 121. The proximal end portion of the second linear control section 105b is fixed to the inner wall surface of the distal end portion of the channel 122. The proximal end portion of the helical tip member 104 of the calculus capturing forceps 101 may be fixed directly to the distal end portion of the endoscope 121.

Further, the first linear control section 105a of the calculus capturing forceps 101 extends to the hand side through the instrument passage channel 122 of the endoscope 121 and is fixed to the hand control section 103.

The distal end face of the endoscope 121 is provided with an image guide 123 and a light guide 124. As shown in FIG. 19B, moreover, the ultrasonic lithotriptic probe 110 is passed through the instrument passage channel 122 of the endoscope 121.

In the calculus capturing forceps 101 of the present embodiment, the hand control section 103 is slid in the axial direction so that the relative positions of the two linear control sections 105a and 105b in their length direction can be changed to increase or decrease the diameter of the helical portion of the helical tip member 104. Therefore, the calculus 113 can be kept fixed until it is pulverized by means of the ultrasonic lithotriptic probe 110 in a manner such that it is fixed in the helical member 104 in front of the instrument passage channel 122 of the endoscope 121 by the same method of the seventh embodiment. Thus, the calculus 113 can be prevented from being moved by a shock without being crushed during the lithotriptic operation. Further, there is no possibility of the calculus 113 being moved away from the ureteroscope 109 by the lithotriptic shock and requiring extra time for repeated approach. Thus, the lithotriptic operation can be carried out efficiently.

According to the present embodiment, in particular, the proximal end portion of the second linear control section 105b of the calculus capturing forceps 101 or the proximal end side of the helical member 104 is fixed to the distal end portion of the endoscope 121. Accordingly, the calculus 113 that is captured in the helical member 104 can be held more easily in front of the instrument passage channel 122. In passing the ultrasonic lithotriptic probe 110 through the channel 122 with the calculus 113 and crushing the captured calculus 113, therefore, the calculus 113 can be prevented from moving away from the endoscope. Thus, the calculus 113 can be crushed and sucked efficiently.

The endoscope (ureteroscope 109) of the seventh embodiment has two channels, while the endoscope 121 of the eighth embodiment has one channel. Alternatively, however, this relation may be reversed.

Figure 20:
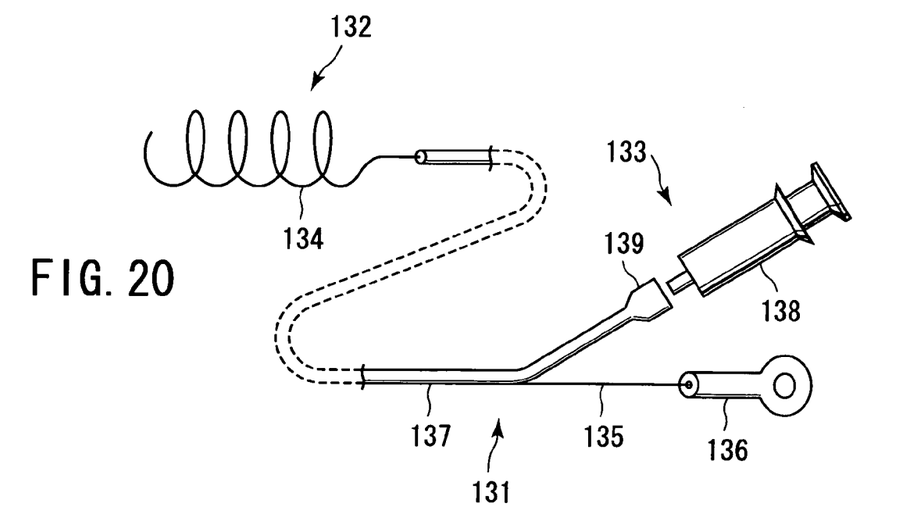
FIG. 20 is a schematic view of a calculus capturing forceps according to a ninth embodiment of the invention.

FIG. 20 shows an outline of a calculus capturing forceps 131 according to a ninth embodiment of the invention. The calculus capturing forceps 131 has a calculus capturing section 132 on the distal end side and a hand control section (regulating means) 133 on the proximal end side.

The calculus capturing section 132 has a wire-shaped tip member 134 that is formed of a shape memory alloy. The shape memory alloy of the tip member 134 is loaded with a shape memory such that it becomes helical when it is heated to a preset or higher temperature or subjected to a magnetic field. According to the present embodiment, the tip member 134 is kept in its initial shape, e.g., the shape of a straight wire, without becoming helical at temperatures ranging from about 30° C. to 38° C. When the tip member 134 is heated to about 40° C. or more, its wire is wound helically.

The distal end portion of a straight wire 135 is connected to the proximal end portion of the tip member 134. The proximal end portion of the wire 135 extends to the hand control section 133 and is coupled with a knob 136.

Further, the wire 135 is passed through an elongate tube 137. The proximal end portion of the tube 137 is provided with a connector portion 139 to which a syringe 138 is removably coupled. The tube 137 contains therein all parts of the wire 135 of the calculus capturing forceps 131 of the present embodiment except the tip member 134 and the knob 136.

The shape of the tip member 134 to be memorized is adjusted to any suitable shape that facilitates the captured calculus 113 to be placed in front of a channel through which the lithotriptic probe of any of lithotriptic means is passed and to be crushed.

The following is a description of the operation of the present embodiment arranged in this manner. In order to fix the calculus 113 by means of the calculus capturing forceps 131 of the present embodiment, the tip member 134 is inserted into the endoscope channel after its shape is first changed into a straight one. Then, the tip member 134 is located around the calculus 113. As this is done, the tip member 134 is located close to the calculus 113 so as to range with it.

Subsequently, the syringe 138 is plugged into the connector portion 139 of the tube 137, and a liquid heated to a suitable temperature of about 40° C. or more is poured from the syringe 138. If this liquid is supplied through the tube 137 to the area around the tip member 134, the tip member 134 is deformed into a helical shape and winds around the calculus 113. Thus, the calculus 113 is captured in the helix of the tip member 134.

If the knob 136 is pulled to the hand side with the helix of the tip member 134 wound around the calculus 113, moreover, the calculus 113 can be brought close to and fixed in a position in front of the channel. In this state, therefore, the lithotriptic probe can be inserted to crush the calculus and suck and recover the resulting fragments.

The tube 137 may be omitted. In this case, the channel of the endoscope is used in place of the tube 137.

Figure 21:
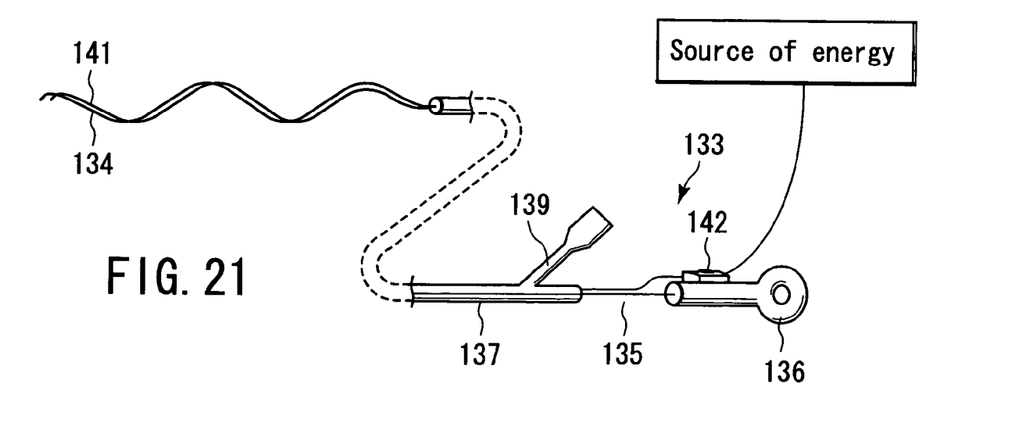
FIG. 21 is a schematic view showing a modification of the calculus capturing forceps of the ninth embodiment.

FIG. 21 shows a modification of the calculus capturing forceps 131 of the ninth embodiment (see FIG. 20). According to this modification, as another method of changing the shape of the tip member 134, a heating element 141, such as a nichrome wire, is attached to the tip member 134 in place of the tube 137. Further, the hand control section 133 may be provided with switch means 142 for controlling the energy supply to the heating element 141.

Figure 22:
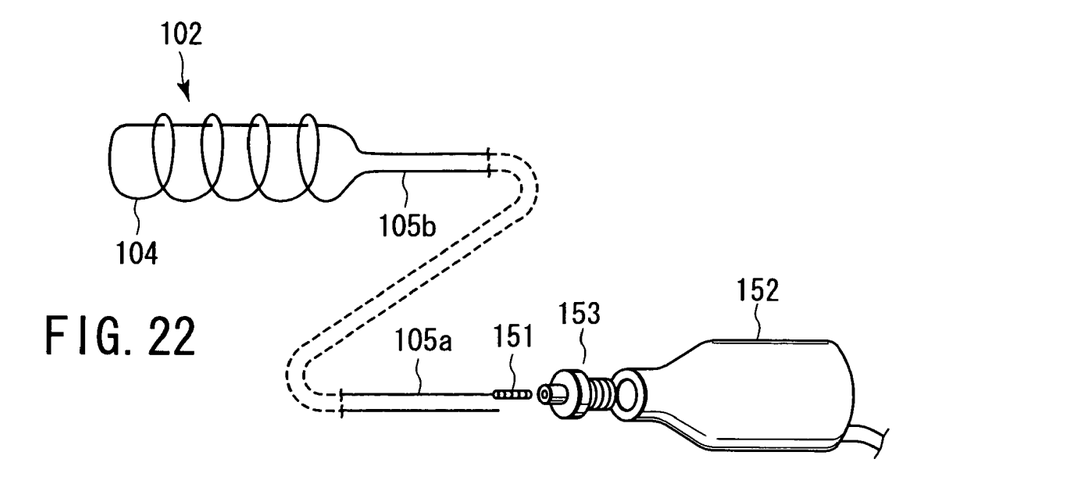
FIG. 22 is a schematic view of a calculus capturing forceps according to a tenth embodiment of the invention.

FIG. 22 shows a tenth embodiment of the invention. According to the present embodiment, an external thread portion 151 is provided on the proximal end portion of the first linear control section 105a of the calculus capturing forceps 101 of the seventh embodiment (see FIGS. 17A and 17B and FIGS. 18A and 18B). The distal end face of a control section body 106 of a hand control section 103 is formed having a tapped hole portion (not shown) that mates with the external thread portion 151.

The external thread portion 151 of the first linear control section 105a can be connected to an ultrasonic vibrator 152. For this connection, the external thread portion 151 may be screwed directly into the ultrasonic vibrator 152. Alternatively, the external thread portion 151 of the first linear control section 105a and the ultrasonic vibrator 152 may be connected to each other by means of an adapter 153.

In the configuration described above, the calculus 113 is subjected to ultrasonic vibration from the ultrasonic vibrator 152 as it is trapped in a helical member 104. By doing this, the helical member 104 can be smoothly wound around the calculus 113 with reduced resistance.

A vibrator for ultrasonic lithotripter may be used as the ultrasonic vibrator 152 that subjects the helical member 104 to ultrasonic vibration by means of the first linear control section 105a.

FIGS. 23A and 23B and FIGS. 24A and 24B show an eleventh embodiment of the invention. A calculus capturing forceps 161 of the present embodiment comprises a cannula 162 and a linear member bundle 163. The linear member bundle 163 is passed through the cannula 162. It can be moved back and forth with respect to the cannula 162.

Figure 24A:
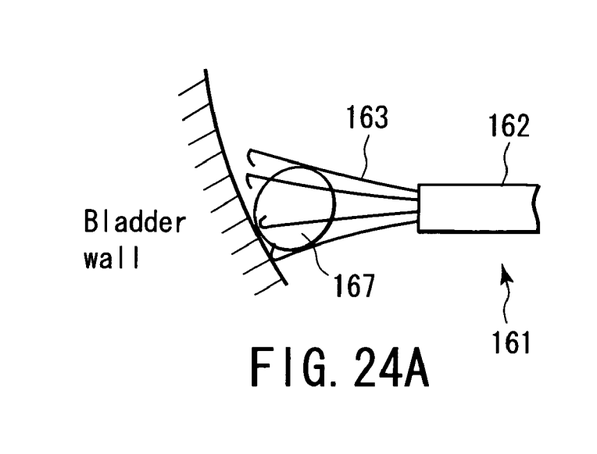
FIG. 24A is a schematic view showing the way the distal end portion of the calculus capturing forceps of the eleventh embodiment is pressed against a calculus.
Figure 24B:
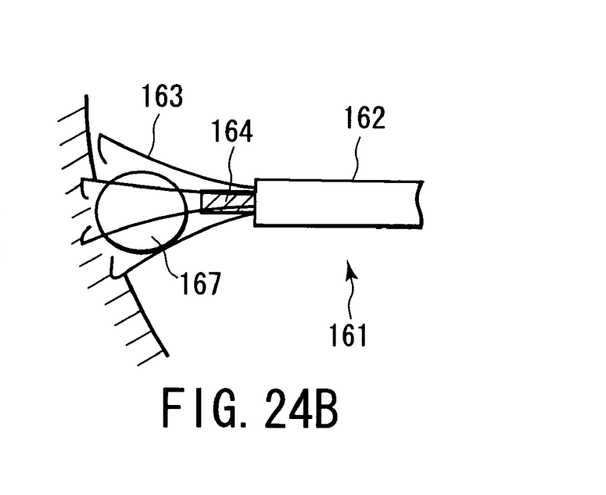
FIG. 24B is a schematic view showing lithotriptic operation.

As shown in FIG. 24B, moreover, a lithotriptic probe 164, such as an ultrasonic lithotripter or kinetic-energy lithotripter, is passed through a space inside the linear member bundle 163 in the cannula 162.

Figure 23A:
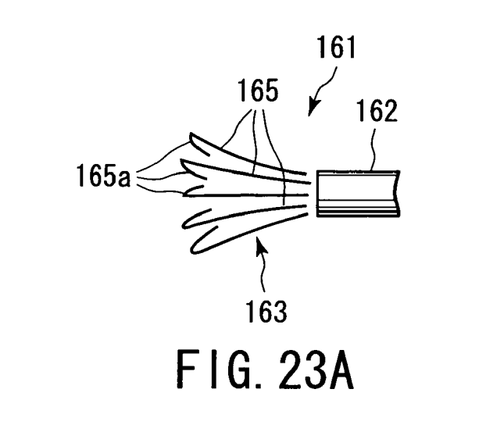
FIG. 23A is a side view of a principal part showing a tip portion of calculus capturing forceps according to an eleventh embodiment of the invention.
Figure 23B:
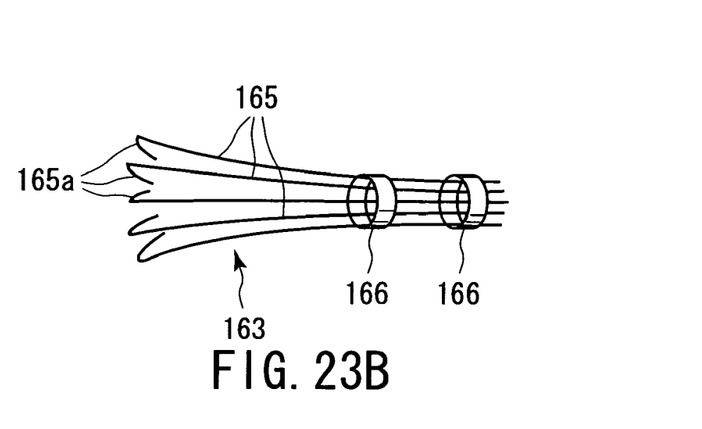
FIG. 23B is a perspective view showing a linear member bundle of the calculus capturing forceps of the eleventh embodiment.

The linear member bundle 163 is composed of a plurality of elastic linear members 165 that are arranged in the shape of a cylinder along the inner peripheral surface of the cannula 162. An inwardly-bent portion 165a is formed on the distal end portion of each linear member 165.

Although the respective distal end portions of the linear members 165 are not fixed, as shown in FIG. 23B, a plurality of fixing rings 166 are mounted on the hand side of the members 165. The linear members 165 are fixedly coupled to one another by means of the rings 166 to maintain the cylindrical shape.

The linear members 165 that constitute the linear member bundle 163 are three or more in number, for example, and preferably, three to eight. Each linear member 165 is formed to have a tendency to bend outward.

The following is a description of the operation of the present embodiment arranged in this manner. In starting the operation of the calculus capturing forceps 161 of the present embodiment, the distal end portion of the linear member bundle 163 is pushed out of the cannula 162. Thereupon, the bend of the linear members 165 is restored by elasticity, so that the distal end part of the bundle 163 spreads. At the same time, the respective distal end portions of the linear members 165 are bent inwardly, so that the distal end part of the linear member bundle 163 is then in the shape of a basket.

If the distal end portion of the calculus capturing forceps 161 is pressed against a calculus 167 in this state, the distal end portion of the linear member bundle 163, spread like a basket as shown in FIG. 24A, captures the calculus 167 therein. If the forceps 161 is then pulled to the hand side, the calculus 167 is fixed in front of the endoscope channel. If the lithotriptic probe 164, e.g., the ultrasonic lithotripter or kinetic-energy lithotripter, is inserted to carry out lithotriptic operation in this state, as shown in FIG. 24B, fragments of the calculus 167 can be sucked and recovered.

If the calculus 167 must be released before the lithotriptic is completed, moreover, the linear member bundle 163 is pulled with a greater force. During this operation, the bent portions 165a on the respective distal ends of the linear members 165, which are bent inward to hold down the calculus 167, are elastically deformed and straightened, so that the calculus 167 can be released.

In the present embodiment, the linear member bundle 163 is located in the cannula 162, and it is inserted together with the cannula 162 in the channel of the endoscope. However, the cannula 162 may be omitted if the endoscope channel is used in place of it.

Figure 25:
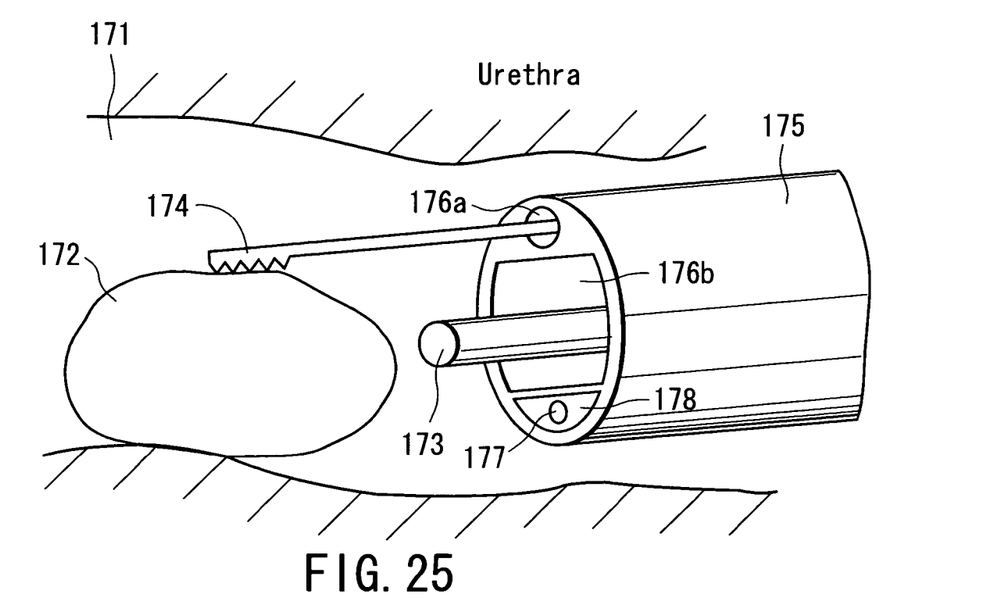
FIG. 25 is a schematic view of a principal part showing a twelfth embodiment of the invention.

FIG. 25 shows a twelfth embodiment of the invention. The present embodiment is provided with a calculus presser 174, which is used to press a calculus 172 in a urethra 171 when the calculus 172 is crushed by means of a lithotriptic probe 173, such as an ultrasonic lithotripter or kinetic-energy lithotripter.

As shown in FIG. 25, the distal end face of an endoscope 175 that is inserted into the urethra 171 is provided with two instrument passage channels 176a and 176b, an image guide 177, and a light guide 178. The calculus presser 174 and the lithotriptic probe 173 are inserted in the channels 176a and 176b, respectively.

The following is a description of the operation of the present embodiment arranged in this manner. In starting the operation of the apparatus of the present embodiment, the distal end portion of the endoscope 175 that is inserted into the urethra 171 is brought close to the calculus 172. In this state, the calculus presser 174 and the lithotriptic probe 173 are inserted through the instrument passage channels 176a and 176b, respectively. Alternatively, the calculus presser 174 and the lithotripic probe 173 may be inserted through one and the same channel.

Then, the calculus presser 174 that is inserted in the instrument passage channel 176a is caused to project to a position above the calculus 172. In this state, the endoscope 175 is rotated clockwise or counterclockwise around its axis. Thus, the calculus 172 can be pressed against the wall of the body cavity and fixed by means of the calculus presser 174.

Subsequently, lithotripsy is carried out by means of the lithotriptic probe 173 in this state. Thus, the calculus 172 can be fixed to the front of the channel 176b of the endoscope 175 as the lithotriptic operation is carried out. After the lithotriptic operation is finished, the calculus presser 174 is drawn out first. Accordingly, there is no possibility of the calculus presser 174 hindering the lithotriptic probe 173 from being drawn out of the body cavity.

Figure 26A:
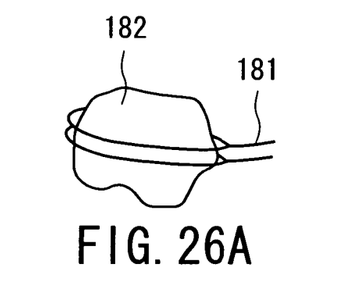
FIG. 26A is a perspective view showing the way a strainer according to a thirteenth embodiment of the invention is attached to a calculus.
Figure 26B:
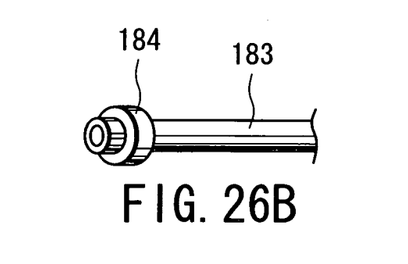
FIG. 26B is a perspective view of a principal part showing a magnet on the distal end of a lithotriptic probe.

FIGS. 26A and 26B show a thirteenth embodiment of the invention. According to the present embodiment, a calculus 182 is fitted with a capture tool 181 of magnetic material, such as a clip or wire, as shown in FIG. 26A. The clip is attached to the calculus 182 by means of a mechanism that drives the clip into the calculus 182 or nips the entire calculus 182 with the clip, for example.

Further, the wire is attached to the calculus 182 by using means that hitches a preformed loop of the wire to the calculus 182, narrows it, and then cuts off the loop at the root.

As shown in FIG. 26B, moreover, a magnet 184 is provided on the distal end of a lithotriptic probe 183.

In starting the operation of the apparatus of the present embodiment, the distal end portion of an endoscope that is inserted into the urethra is brought close to the calculus 182. In this state, the lithotriptic probe 183 is inserted through an instrument passage channel of the endoscope. Subsequently, the magnetic capture tool 181 that is attached to the calculus 182 is attracted to the magnet 184 on the distal end of the lithotriptic probe 183.

Thus, the calculus 182 is drawn near the front side of the instrument passage channel of the endoscope so that the lithotriptic probe 183 can be easily brought into contact with the calculus 182. Further, the calculus 182 can be prevented from being wide apart from the probe 183 during lithotriptic operation, so that the calculus 182 can be crushed efficiently.

In attaching the magnet 184 to the distal end of the lithotriptic probe 183, moreover, the magnet 184 is situated just behind the distal end of the probe 183. Thus, the force of attraction of the magnet 184 can be secured, and the magnet 184 can be prevented from running against the calculus 182 and breaking during the lithotriptic operation.

According to the present embodiment, therefore, the calculus 182 can be attracted so that it is situated substantially on the front face of the channel of the endoscope as it is crushed. Thus, the same effect of the means described in Patent Document 7 can be obtained by a different method.

Figure 27A:
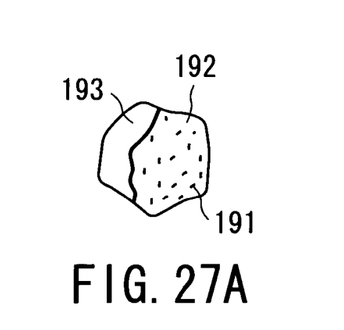
FIG. 27A is a perspective view showing the way an adhesive agent mixed with a magnetic substance according to a fourteenth embodiment of the invention is spread on the surface of a calculus.
Figure 27B:
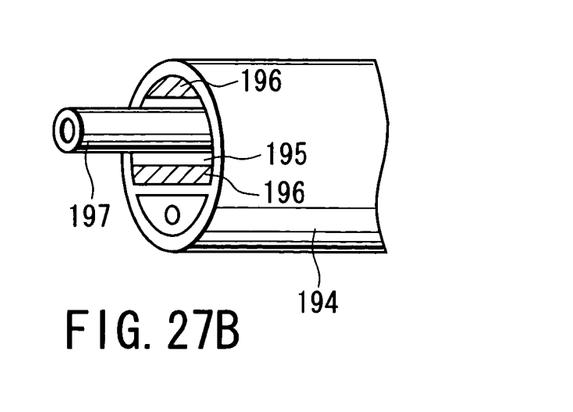
FIG. 27B is a perspective view of a principal part showing magnets fixed to the distal end portion an endoscope.

FIGS. 27A and 27B show a fourteenth embodiment of the invention. According to the present embodiment, an adhesive agent 192, such as fibrin glue mixed with a magnetic substance 191 or an acrylic adhesive agent, is spread on the surface of a calculus 193, as shown in FIG. 27A. At the distal end portion of an endoscope 194, moreover, magnets 196 are fixed to peripheral wall portions of an instrument passage channel 195, as shown in FIG. 27B.

The magnetic substance 191 of the adhesive agent 192 that is attached to the calculus 193 can be attracted to the magnets 196 at the distal end portion of the endoscope 194. In the present embodiment, as in the thirteenth embodiment (see FIGS. 26A and 26B), therefore, the calculus 193 is drawn near the front side of the instrument passage channel 195 of the endoscope 194 so that the lithotriptic probe 197 can be easily brought into contact with the calculus 193. Further, the calculus 193 can be prevented from being wide apart from the probe 197 during lithotriptic operation, so that the calculus 193 can be crushed efficiently.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A calculus manipulation apparatus comprising: first and second ultrasonic generator elements which generate ultrasonic vibration; a first transmission probe having a proximal end portion connected to the first ultrasonic generator element and a hollow portion in the form of a through hole; a tip manipulator element which is provided on the distal end portion of the first transmission probe and brought into contact with a calculus, the tip manipulator element receiving ultrasonic vibration from the ultrasonic generator elements through the probe; and a second transmission probe capable of being passed through the hollow portion of the first transmission probe, the second probe having a piercer section on the distal end portion thereof to which ultrasonic vibration is transmitted from the second ultrasonic generator element and which is stabbed into the calculus and a calculus fixing section which fixes the calculus to the distal end portion.

2. A calculus manipulation apparatus comprising: first and second ultrasonic generator elements which generate ultrasonic vibration; a first transmission probe having a proximal end portion connected to the first ultrasonic generator element and a hollow portion in the form of a through hole; a tip manipulator element which is provided on the distal end portion of the first transmission probe and brought into contact with a calculus, the tip manipulator element receiving ultrasonic vibration from the ultrasonic generator elements through the probe; and a second transmission probe capable of being passed through the hollow portion of the first transmission probe, the second probe having a piercer section on the distal end portion thereof to which ultrasonic vibration is transmitted from the second ultrasonic generator element and which is stabbed into the calculus and a calculus fixing section which fixes the calculus to the distal end portion, wherein the calculus fixing section has means which stops the second ultrasonic generator element with the piercer section in the calculus.

* * * * *